US012605499B2

(12) United States Patent
Vale et al.

(10) Patent No.: US 12,605,499 B2
(45) Date of Patent: Apr. 21, 2026

(54) SYNCHRONIZED ASPIRATION SYSTEM WITH CATHETER SENSORS FOR REMOVAL OF ACUTE BLOCKAGES FROM BLOOD VESSELS

(71) Applicants: Neuravi Limited, Galway (IE); Biosense Webster (Israel) Ltd., Yokneam (IL)

(72) Inventors: David Vale, Barna (IE); Avi Shalgi, Yokneam Illit (IL); Ray McCarthy, Galway (IE); Michael Gilvarry, Headford (IE); Brendan Casey, Barna (IE)

(73) Assignees: Neuravi Limited, Galway (IE); Biosense Webster (Israel) Ltd., Yokneam (IL)

( * ) Notice: Subject to any disclaimer, the term of this patent is extended or adjusted under 35 U.S.C. 154(b) by 1007 days.

(21) Appl. No.: 17/743,121

(22) Filed: May 12, 2022

(65) Prior Publication Data

US 2023/0364319 A1 Nov. 16, 2023

(51) Int. Cl.
*A61B 17/22* (2006.01)
*A61M 1/00* (2006.01)
A61M 25/01 (2006.01)

(52) U.S. Cl.
CPC ..... *A61M 1/84* (2021.05); *A61B 2017/22079* (2013.01); *A61B 2217/005* (2013.01); *A61M 2025/0166* (2013.01)

(58) Field of Classification Search
CPC ........... A61B 2017/00026; A61B 2017/00703; A61B 2017/22079; A61B 2090/064; A61M 2025/0166
See application file for complete search history.

(56) References Cited

U.S. PATENT DOCUMENTS

| | | | |
|---|---|---|---|
| 4,445,509 | A | 5/1984 | Auth |
| 8,100,874 | B1 | 1/2012 | Jordan et al. |

(Continued)

FOREIGN PATENT DOCUMENTS

| | | |
|---|---|---|
| CA | 2 815 186 C | 12/2015 |
| CN | 1216929 A | 5/1999 |

(Continued)

OTHER PUBLICATIONS

International Search Report and Written Opinion issued in International Patent Application No. PCT/EP2023/062599 dated Jul. 28, 2023.

(Continued)

*Primary Examiner* — Deanna K Hall
(74) *Attorney, Agent, or Firm* — Troutman Pepper Lock LLP

(57) ABSTRACT

An aspiration catheter for assisting in the retrieval of a clot from a vessel of a patient including at least one electrode pair and a first pressure sensor positioned within an inner lumen of the aspiration catheter and a second and third pressure sensor positioned on an exterior surface of the aspiration catheter. The electrode pair and pressure sensors are in electrical communication with a control console. The control console is configured to modulate an aspiration vacuum pressure waveform pattern applied through the aspiration catheter based on electrical and pressure inputs from the one or more sensors, and optionally based on a blood pressure waveform pattern of the patient.

9 Claims, 6 Drawing Sheets

(56) References Cited

U.S. PATENT DOCUMENTS

| | | | |
|---|---|---|---|
| 11,464,528 | B2 | 10/2022 | Brady et al. |
| 2005/0054971 | A1 | 3/2005 | Steen et al. |
| 2005/0192548 | A1 | 9/2005 | Dolliver et al. |
| 2007/0060888 | A1 | 3/2007 | Goff et al. |
| 2010/0174170 | A1 | 7/2010 | Razavi |
| 2013/0165944 | A1 | 6/2013 | Gal et al. |
| 2013/0304003 | A1 | 11/2013 | Stiehl |
| 2015/0342682 | A1 | 12/2015 | Bowe |
| 2016/0166265 | A1 | 6/2016 | Nita |
| 2016/0184562 | A1 | 6/2016 | Ludin et al. |
| 2017/0150993 | A1 | 6/2017 | Ganz et al. |
| 2017/0296712 | A1 | 10/2017 | Anton |
| 2017/0354777 | A1 | 12/2017 | Ofek et al. |
| 2019/0381223 | A1 | 12/2019 | Culbert et al. |
| 2021/0393907 | A1 | 12/2021 | Ahmed et al. |
| 2022/0409857 | A1* | 12/2022 | Saadat ........... A61B 17/320783 |

FOREIGN PATENT DOCUMENTS

| | | | |
|---|---|---|---|
| CN | 1768874 | A | 5/2006 |
| CN | 101088472 | A | 12/2007 |
| CN | 201079423 | Y | 7/2008 |
| CN | 101259296 | A | 9/2008 |
| CN | 101868280 | A | 10/2010 |
| CN | 102209516 | A | 10/2011 |
| CN | 103932756 | A | 7/2014 |
| JP | 9-53568 | A | 2/1997 |
| JP | 2000-139934 | A | 5/2000 |
| WO | 2014/151209 | A1 | 9/2014 |
| WO | 2017/147493 | A1 | 8/2017 |
| WO | 2021/074265 | A1 | 4/2021 |
| WO | 2021/222157 | A1 | 11/2021 |

OTHER PUBLICATIONS

Office Action and Search Report issued in Chinese Patent Application No. 201780059366.8 dated Apr. 22, 2022, English translation of Search Report.

Chinese Office Action and Search Report issued in Chinese Patent Application No. 201780059366.8 dated Jun. 15, 2021, with English translation of Search Report.

International Search Report and Written Opinion for corresponding International Application No. PCT/EP2017/068759 Issued Feb. 1, 2018.

Notification of Reasons for Refusal issued in corresponding Japanese Patent Application No. 2019-504107 dated May 25, 2021 (English translation only).

* cited by examiner

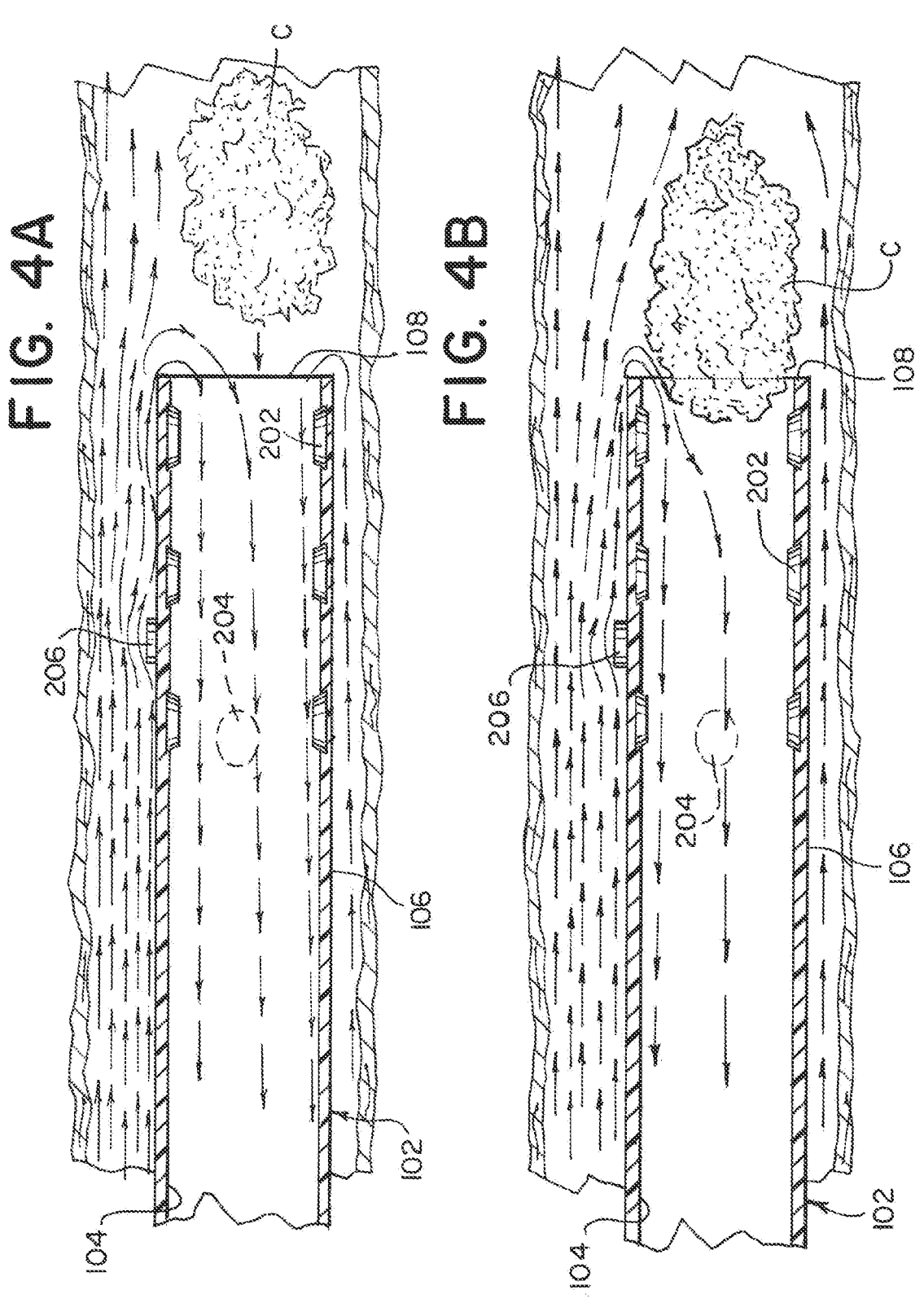

SYNCHRONIZED ASPIRATION SYSTEM WITH CATHETER SENSORS FOR REMOVAL OF ACUTE BLOCKAGES FROM BLOOD VESSELS

FIELD

This disclosure relates generally to devices and methods of detecting and removing acute blockages from blood vessels, and more particularly to aspiration catheters having sensors to assist in providing direct feedback while removing acute blockages from blood vessels.

BACKGROUND

Acute obstructions may include clot, misplaced devices, migrated devices, large emboli and the like. Thromboembolism occurs when part or all of a thrombus breaks away from the blood vessel wall. The clot (now called an embolus) is then carried in the direction of blood flow. If the clot lodges in the cerebral vasculature, an ischemic stroke may result. If the clot originates in the venous system or in the right side of the heart and lodges in a pulmonary artery or branch, a pulmonary embolism may result. Clots may also develop and block vessels locally without being released in the form of an embolus—this mechanism is common in the formation of coronary blockages.

Clot retrieval catheters and devices are used in mechanical thrombectomy for endovascular intervention, often in cases where patients are suffering acute ischemic stroke (AIS), myocardial infarction (MI), and pulmonary embolism (PE). Accessing remote areas such as the neurovascular bed is challenging with conventional technology, as the target vessels are small in diameter, distant relative to the site of insertion, and are highly tortuous.

Conventional clot retrieval catheters, especially those for operating in the neurovascular blood vessels, lack direct feedback to medical professionals regarding the degree of or quality of the clot entrapment at the occlusion site, therefore medical professionals must make assumptions based on indirect feedback from the catheter (e.g., if no blood is moving through the catheter, whether the clot is stuck at the end of the catheter, the vessel collapsed, or the catheter is attached to a vessel wall).

The disclosed design is aimed at providing an improved clot retrieval catheter which addresses the above-stated deficiencies.

SUMMARY

Examples presented herein include devices and methods for removing acute blockages from blood vessels during intravascular medical treatments. More specifically, the present disclosure relates to a clot retrieval catheter system having sensors to assist in providing direct feedback during intravascular medical treatments. Examples disclosed herein are generally aimed at providing direct feedback to medical professionals regarding the engagement with a clot and fluid dynamics in and around the catheter during catheter delivery, at the occlusion site, during aspiration of the clot, and/or during withdrawal of the catheter.

An example system for retrieving an obstruction in a blood vessel can include an aspiration catheter having at least one electrode pair, a first pressure sensor, a second pressure sensor, and a third pressure sensor. The electrode pair can be positioned on a first side of a wall that defines an inner lumen of the aspiration catheter. The inner lumen can extend proximal along a longitudinal axis between a distal tip and a proximal hub. The first pressure sensor can be positioned at a distal portion proximal the distal tip and within the inner lumen of the aspiration catheter. The second pressure sensor can be positioned at a distal portion proximal the distal tip on an opposed side of the wall that defines an exterior surface of the aspiration catheter. The third pressure sensor can be positioned at a proximal portion of the aspiration catheter on the exterior surface.

In some examples, the at least one electrode pair can be configured to transmit an electrical input to a control console. The electrical input can include a change in conductivity in blood or another fluid flowing inside the inner lumen of the aspiration catheter. When the distal tip of the aspiration catheter is near the clot, the at least one electrode pair can be configured to detect the clot within the blood flowing inside the inner lumen of the aspiration catheter. When the distal tip of the aspiration catheter is engaged with the clot, the at least one electrode pair can be configured to monitor the clot as the aspiration catheter is moved about the vessel.

In some examples, the first pressure sensor can be configured to transmit a first pressure input to a control console. The second pressure sensor can be configured to transmit a second pressure input to the control console. The third pressure sensor can be configured to transmit a third pressure input to the control console. The first, second, and third pressure inputs can be different.

In some examples, when the distal tip of the aspiration catheter is near the clot, the first pressure input and the second pressure input together can generate a pressure measurement of an antegrade flow rate around the aspiration catheter in the vessel.

In some examples, the control console can be further configured to modulate an aspiration by applying an oscillating vacuum waveform based on pressure input from one or more pressure sensors. The control unit can be further configured to modulate an aspiration to a waveform of a blood pressure of a patient by applying an oscillating vacuum waveform in phase with the blood pressure waveform of the patient. The control unit can be further configured to modulate an aspiration to a waveform of a blood pressure of a patient by applying an oscillating vacuum waveform out of phase with the blood pressure waveform of the patient.

An example system for retrieving an obstruction in a blood vessel can include an outer catheter and an inner catheter. The inner catheter can be disposed in a lumen of the outer catheter. The inner catheter can include at least one electrode pair, at least one internal pressure sensor, and at least one external pressure sensor. The electrode pair can be positioned on an inner lumen of the inner catheter. The internal pressure sensor can be positioned on the inner lumen of the inner catheter. The external pressure sensor can be positioned on an exterior surface of the inner catheter.

In some examples, the system can also include a seal located on the exterior surface of the inner catheter. The seal can be capable of sealing against the lumen of the outer catheter such that an aspiration applied through the outer catheter can be transferred to the inner catheter.

The system can further include a control console configured to modulate an aspiration. The control console can modulate an aspiration by applying a vacuum waveform pattern through the inner catheter based on at least one input from the at least one electrode pair, the at least one internal pressure sensor, or the at least one external pressure sensor. The at least one external pressure sensor can be configured to transmit a pressure input correlated to a blood pressure of the patient. The control console can be further configured to modulate the aspiration by applying a vacuum waveform pattern in phase with a blood pressure waveform of the patient. The control console can be further configured to modulate the aspiration by applying a vacuum waveform pattern out of phase with a blood pressure waveform of the patient.

An example method for manufacturing an aspiration catheter can include positioning a first pressure sensor on an internal lumen of a distal portion of an aspiration catheter. The method can include positioning a second pressure sensor on an external surface of the distal portion of the aspiration catheter. The method can also include positioning a third pressure sensor on the external surface of a proximal portion of the aspiration catheter.

In some instances, the method can further include detecting, by the first pressure sensor, a pressure change within the internal lumen of the aspiration catheter when the aspiration catheter is engaged with a clot in a vessel. The method can include detecting, by the second pressure sensor, the pressure change within the vessel external to the aspiration catheter when the aspiration catheter is engaged with the clot. The method can also include generating a pressure measurement of a flow rate around the aspiration catheter in the vessel.

In some examples, the method can further include applying a vacuum waveform pattern through the aspiration catheter based on the pressure change from at least one pressure sensor.

The method can further include positioning at least one electrode pair on the internal lumen of the distal portion of the aspiration catheter. The method can include detecting, by the at least one electrode pair, a conductivity change in a fluid flowing inside the aspiration catheter when the aspiration catheter is engaged with a clot.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The above and further aspects of this disclosure are further discussed with the following description of the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation. It is expected that those of skill in the art can conceive of and combining elements from multiple figures to better suit the needs of the user.

FIGS. 4A through 4C illustrate side views of an example clot receptor device and fluid dynamics in and around the device, according to aspects of the present disclosure.

FIG. 6 is a flow diagram illustrating a method of manufacturing a clot retrieval system, according to aspects of the present disclosure.

DETAILED DESCRIPTION

Figure 1A:
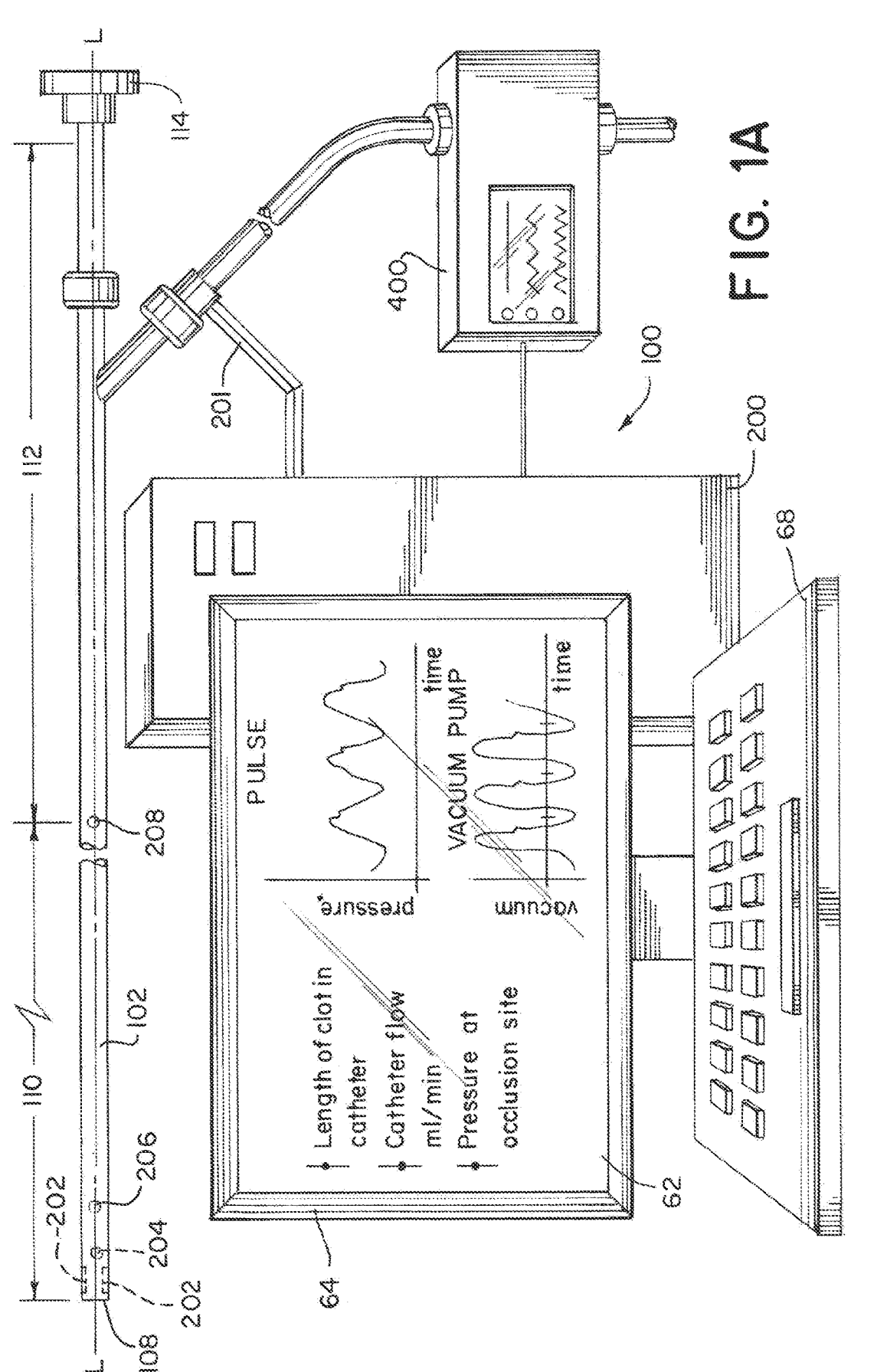
FIG. 1A is a schematic pictorial illustration of an example clot retrieval system having an aspiration catheter with sensors, a sensor console, and an aspiration pump, according to aspects of the present disclosure.

The herein disclosed solution is directed to devices and systems capable of providing direct feedback to a medical professional relating to the degree of or quality of entrapment of a clot within the device. Such devices and systems can also provide fluid dynamic feedback in the catheter and vessel at multiple points during the process of retrieving a clot, including, but not limited to, during catheter delivery, at the occlusion site, during aspiration of the clot, or during withdrawal of the catheter. Additionally, such devices and systems can control an aspiration pump such that an optimized thrombectomy can be performed. Controlling the aspiration process can be based on fluid dynamic feedback measured along the device at varied points during the process, including locally at the occlusion site, systemically at proximal locations in the vessel, and within the catheter lumen. Fluid dynamics and clot entrapment feedback can offer substantially greater aspiration efficiency and reduce the risk of emboli migration. Such advantages can also be especially beneficial in the case of stroke intervention procedures, where vessels in the neurovascular bed are particularly small and circuitous, and as a result a clot retrieval catheter with sensors that can provide direct feedback and fluid dynamics through tortuous vessels can increase the aspiration efficiency.

These improvements can lead to safe and more rapid access of a catheter and other devices to complex areas in order to remove occlusions and shorten procedure times. While the description is in many cases in the context of mechanical thrombectomy treatments, the systems and methods can be adapted for other procedures and in other body passageways as well.

Accessing the various vessels within the vascular system, whether they are coronary, pulmonary, or cerebral, involves well-known procedural steps and the use of a number of conventional, commercially-available accessory products. These products, such as angiographic materials, rotating hemostasis valves, and guidewires are widely used in laboratory and medical procedures.

It should also be noted that, as used in the specification and the appended claims, the singular forms "a," "an" and "the" include plural references unless the context clearly dictates otherwise. References to a composition containing "a" constituent is intended to include other constituents in addition to the one named. Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

Various devices and methods are disclosed for providing an electrically actuated clot retrieval catheter, and examples of the devices and methods will now be described with reference to the accompanying figures.

FIG. 1A is a schematic, pictorial illustration of a system 100 having an aspiration catheter 102 with sensors. In examples described hereinbelow, the clot retrieval system 100 can be used for diagnostic or therapeutic treatment, such as for performing thrombectomy procedures in a vessel of a patient. Alternatively, the clot retrieval system 100 may be used for other therapeutic and/or diagnostic purposes in the brain, heart, or in other body organs.

The system 100 can include an aspiration catheter 102 for assisting in retrieval of a clot from a vessel of a patient. The aspiration catheter 102 can include at least one electrode pair 202, a first pressure sensor 204, a second pressure sensor 206, and a third pressure sensor 208, as described in the description referencing FIGS. 2A and 2B hereinbelow. During a medical procedure, a medical professional can insert the aspiration catheter 102 through the vascular system of the patient so that a distal tip 108 of the aspiration catheter 102 approaches a clot. Upon the distal tip 108 engaging with the clot, the medical professional can initiate aspiration through the catheter 102 into a syringe (not illustrated) or a pump 400. To start performing aspiration of the clot, the medical professional can manipulate the vacuum pressure and/or pressure waveform pattern of an aspiration pump 400 based on the input from the electrode pairs 202 and/or the pressure sensors 204, 206, 208 so that the distal tip 108 of the catheter 102 engages the clot.

Figures 1B, 2A, 2B:
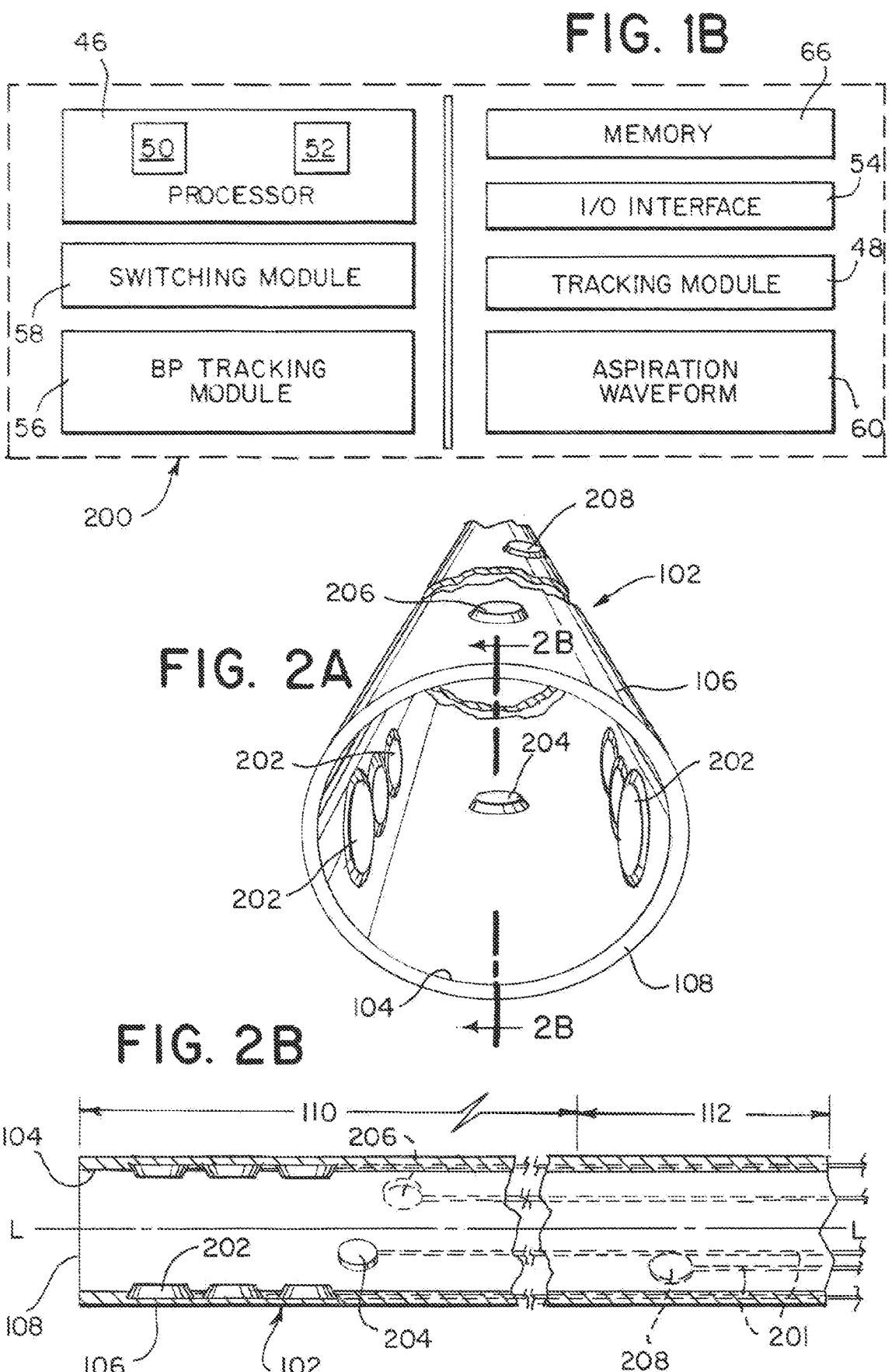
FIG. 1B is a block diagram of an illustrative computer system architecture of an example clot retrieval system 200, according to aspects of the present disclosure.
FIG. 2A illustrates a front view of a distal tip of an example clot receptor device showing internal electrodes, according to aspects of the present disclosure.
FIG. 2B illustrates a sectional side view of an example clot retrieval system, according to aspects of the present disclosure.

In the configuration shown in FIGS. 1A and 1B, a control console 200 is connected, by one or more cables 201, to the sensors positioned on and within the aspiration catheter 102, as depicted more clearly in FIGS. 2A and 2B. Control console 200 includes a processor 46 that, in conjunction with a tracking module 48, can determine location coordinates of the distal tip 108 and/or a distal portion 110 of the catheter 102 inside the patient. Location coordinates of the distal portion 110 of the catheter 102 can be determined based on electromagnetic position sensor output signals provided from the distal portion 108 of the catheter 02 when in the presence of a generated magnetic field. Location coordinates can additionally, or alternatively be based on impedances and/or currents measured between adhesive skin patches positioned on the patient and electrode pairs 202 that are affixed to the catheter 102. In addition to being used as location sensors during a medical procedure, the electrode pairs 202 may perform other tasks such electrical impendence measurements and/or compositional measurements of objects flowing within the catheter 102. Such a determination is typically after a calibration process relating the impedances or currents to known locations of the distal portion 110 has been performed. For instance, the electrode pairs 202, through electrical impedance and resistivity measurements, can be configured to detect a signal when the clot enters into the distal portion 110 of the catheter 102. A change in resistivity of plasma is expected due to a change in the concentration of coagulation factors. In addition, due to the location of the electrode pairs 202 at the distal portion 110 of the catheter 102, a clot's time, size, and location could be characterized by the higher local resistivity as the clot approaches and passes through the electrode pairs 202. As appreciated by a person of skill in the art, an increase in fibrin, a prominent component in thrombi, would generate a change in the resistivity of blood flowing between the electrode pairs 202.

Processor 46 may include real-time noise reduction circuitry 50 typically configured as a field programmable gate array (FPGA), followed by an analog-to-digital (A/D) signal conversion integrated circuit 52. The processor 46 can be programmed to perform one or more algorithms and uses circuitry 50 and circuit 52 as well as features of modules to enable the medical professional to perform the thrombectomy procedure.

Control console 200 also includes an input/output (I/O) communications interface 54 that enables control console 200 to transfer signals from, and/or transfer signals to the one or more electrode pairs 202 and pressure sensors 204, 206, 208. In an example implementation, the communication interface 54 may provide functions for rendering video, graphics, images, text, other information, or any combination thereof on a display interface 64. In one example, the communication interface 54 may include a serial port, a parallel port, a general-purpose input and output (GPIO) port, a game port, a universal serial bus (USB), a micro-USB port, a high-definition multimedia (HDMI) port, a video port, an audio port, a Bluetooth port, a near-field communication (NFC) port, another like communication interface, or any combination thereof. In one example, a display interface 64 may be operatively coupled to a local display, such as a touch-screen display associated with a mobile device. In another example, the display interface 64 may be configured to provide video, graphics, images, text, other information, or any combination thereof for an external/remote display that is not necessarily connected to the mobile computing device. In one example, a desktop monitor may be utilized for mirroring or extending graphical information that may be presented on a mobile device. In another example, the display interface 64 may wirelessly communicate, for example, via the network connection interface such as a Wi-Fi transceiver to the external/remote display.

In the configuration shown in FIG. 1B, control console 200 additionally includes a blood pressure (BP) tracking module 56 and a switching module 58. The BP tracking module 56 can be configured to measure and monitor systemic blood pressure from a pressure sensor positioned on an external surface 106 of the catheter 102 near the Internal Carotid Artery (ICA) of the patient, as described in more detail below. In some examples, as provided in FIG. 5, the aspiration catheter 102 can be delivered through an outer catheter or a base catheter. The exit of the outer catheter can be positioned near the ICA such that the pressure sensor on the aspiration catheter 102 (the therapeutic catheter supported by the base catheter in this example) is outside of the base catheter and near the ICA. This pressure sensor can be used in conjunction with the BP tracking module 56 to adjust the vacuum pump pressure waveform pattern so that it matches (either in-phase or out-of-phase) the patient's blood pressure waveform. Alternatively, or in addition thereto, adhesive skin patches worn by the patient can be used in conjunction with the BP tracking module 56 to measure the patient's blood pressure and adjust the vacuum pump pressure waveform pattern to be either in-phase or out-of-phase with the blood pressure waveform pattern. BP tracking module 56 can be configured to generate aspiration pump pressure waveform patterns including oscillating waveforms, square waveforms, or linear waveforms (e.g., pulsed suction or continuous suction). In some examples, the pressure sensor can also be used to evaluate the effect of another device, such as a balloon guide catheter or stentriever, in reducing antegrade blood pressure in the distal ICA.

Based on signals received from the one or more electrode pairs 202 and/or the pressure sensors 204, 206, 208, processor 46 can be configured to generate procedure data 62 indicative of the procedure, such as, for example, a summary of the thrombectomy procedure, e.g., whether the clot is engaged, the length and/or composition of the clot in the catheter 102, the fluid dynamics within and around the catheter 102, or the pressure at the occlusion site. During the procedure, processor 46 can present the procedure data 62 to the medical professional on a display interface 64, and store data representing the procedure data 62 in a memory 66. Memory 66 may include any suitable volatile and/or non-volatile memory, such as random-access memory or a hard disk drive.

In some examples, the medical professional can manipulate the procedure data 62 using one or more input devices 68. In alternative examples, display interface 64 may include a touchscreen that can be configured to accept inputs from the medical professional in addition to presenting any procedure data 62. It is understood that a user interface can be accessed on various devices (e.g., laptop computer, tablet, etc.) and be embodied in various forms. As desired, implementations of the disclosed technology may include a computing device with more or less of the components illustrated in FIG. 1. It will be understood that the architecture of the control console 200 is provided for example purposes only and does not limit the scope of the various implementations of the present disclosed systems, methods, and computer-readable mediums.

Aspiration pump 400 can be configured to create a suction force to assist in engaging and removing the clot during the thrombectomy procedure. The aspiration pump 400 can be a centrifugal pump, a rotary pump, a peristaltic pump, a roller pump, or other suitable form of pump known in the art. In some instances, as described above, the pump 400 may be controlled by the control console 200 via the I/O communications interface 54. The control console 200 may be operated by the medical professional to adjust the speed, pressure, waveform pattern, or other attributes of the pump 400 during the medical procedure. The control console 200 may receive input from the medical professional to control the pump 400 via the input devices 68 or on a separate aspiration pump input via dials, touch screens, buttons, or levers for adjusting pump speed or another pump variable. Alternatively, or in addition thereto, the BP tracking module 56 and switching module 58 can be configured to adjust the speed, pressure, waveform pattern, or other attributes of the pump 400 to match that of the patient's blood pressure waveform pattern, as will be described in more detail below. In some examples, the control console 200 and pump 400 may integrated as a single device. Pump 400 can be configured to generate a negative (suction) pressure sufficient to cause aspiration of the patient's blood through aspiration catheter 102 during use. The pump 400 can be capable of producing negative pressures from 0 mmHg to about −400 mmHg (e.g., from about 0 mmHg to about −350 mmHg, from about 0 mmHg to about −300 mmHg, from about 0 mmHg to about −250 mmHg, from about 0 mmHg to about −200 mmHg, from about 0 mmHg to about −150 mmHg, and from about 0 mmHg to about −100 mmHg).

FIG. 2A provides a front view of the aspiration catheter 102 with sensors for assisting in retrieval of a clot from a vessel of a patient. The aspiration catheter 102 can include at least one electrode pair 202, a first pressure sensor 204, a second pressure sensor 206, and a third pressure sensor 208. As shown in FIG. 2B, the electrode pair 202 can be positioned on a first side of a wall that defines an inner lumen 104 extending proximally along a longitudinal axis L-L of the aspiration catheter 102. The electrode pair 202 can be positioned between a distal tip 108 and a proximal hub 114 (shown in FIG. 1). The first pressure sensor 204 can be positioned within the inner lumen 104 of the aspiration catheter 102 at a distal portion 110 proximal the distal tip 108. The second pressure sensor 206 can be positioned at the distal portion 110 on an exterior surface 106 of the aspiration catheter 102 on a side of the wall opposing the inner lumen 104. The third pressure sensor 208 can also be positioned on the exterior surface 106 of the aspiration catheter 102 and at a proximal portion 112 proximal the position of the second pressure sensor. The electrode pair 202 and pressure sensors 204, 206, 208 can be in electrical communication with the control console 200 (not pictured).

FIG. 2B illustrates a sectional side view of the distal tip 108 of the aspiration catheter 102. As shown, the catheter 102 can include at least one electrode pair 202 and the first pressure sensor 204 positioned within the inner lumen 104 and the second and third pressure sensors 206, 208 positioned on the external surface 106.

The aspiration catheter 102 can include any suitable number of electrode pairs 202, such as, for example, three electrode pairs 202 as depicted in FIGS. 2A and 2B. In some examples, each electrode of a pair can be positioned facing the other electrode pair. As shown in FIG. 2B, the electrode pairs 202 can be positioned in a linear series within the inner lumen 104 starting near the distal tip 108 and traveling proximally toward the proximal portion 112 of the aspiration catheter 102. Although not depicted, the electrode pairs 202 can be offset from neighboring electrode pairs such that the series of electrode pairs are non-linear within the inner lumen 104. The electrode pairs 202 can be configured to transmit an electrical input from the distal tip 108 of the aspiration catheter 102 to the control console 200.

In addition to electrical input from the inner lumen 104 of the distal tip 108, the first pressure sensor 204 can operate using piezo-electric, piezo-resistive, and/or piezo-optic effects to measure an internal pressure within the inner lumen 104. Similarly, the second and third pressure sensors 206, 208 can function the same or similar to the first pressure sensor 204 to measure a pressure of the vessel from fluid, tissue, or other external pressures on the external surface 106 of the catheter 102. Any of the pressure sensors can measure, detect, or monitor the pressure being applied and convert the information into an electrical output signal to the control console 200. The pressure sensors can include internal analog amplifiers either varying in voltage, i.e., +/−10 V, or varying current, i.e., +/−1-20 mA output. In some examples, the pressure sensors can include digital or USB pressure sensor amplifiers. The differential pressure within the catheter 102 and/or within the vessel (external the catheter) can be determined by the measurement of the pressure difference between two pressure values or two pressure points in the system. The differential pressure can provide the medical professional with information regarding the flow of blood within either the vessel or within the catheter.

As would be appreciated by one of skill in the relevant art, the combination of electrical and pressure sensors along various points of an aspiration catheter can provide direct feedback to the medical professional regarding the engagement of the aspiration catheter with the clot. In addition, fluid dynamics within and around the aspiration catheter can provide insight regarding how occlusive the catheter is in the vessel during catheter delivery, at the occlusion site, during aspiration, and/or during withdrawal of the catheter.

Figures 3A, 3B:
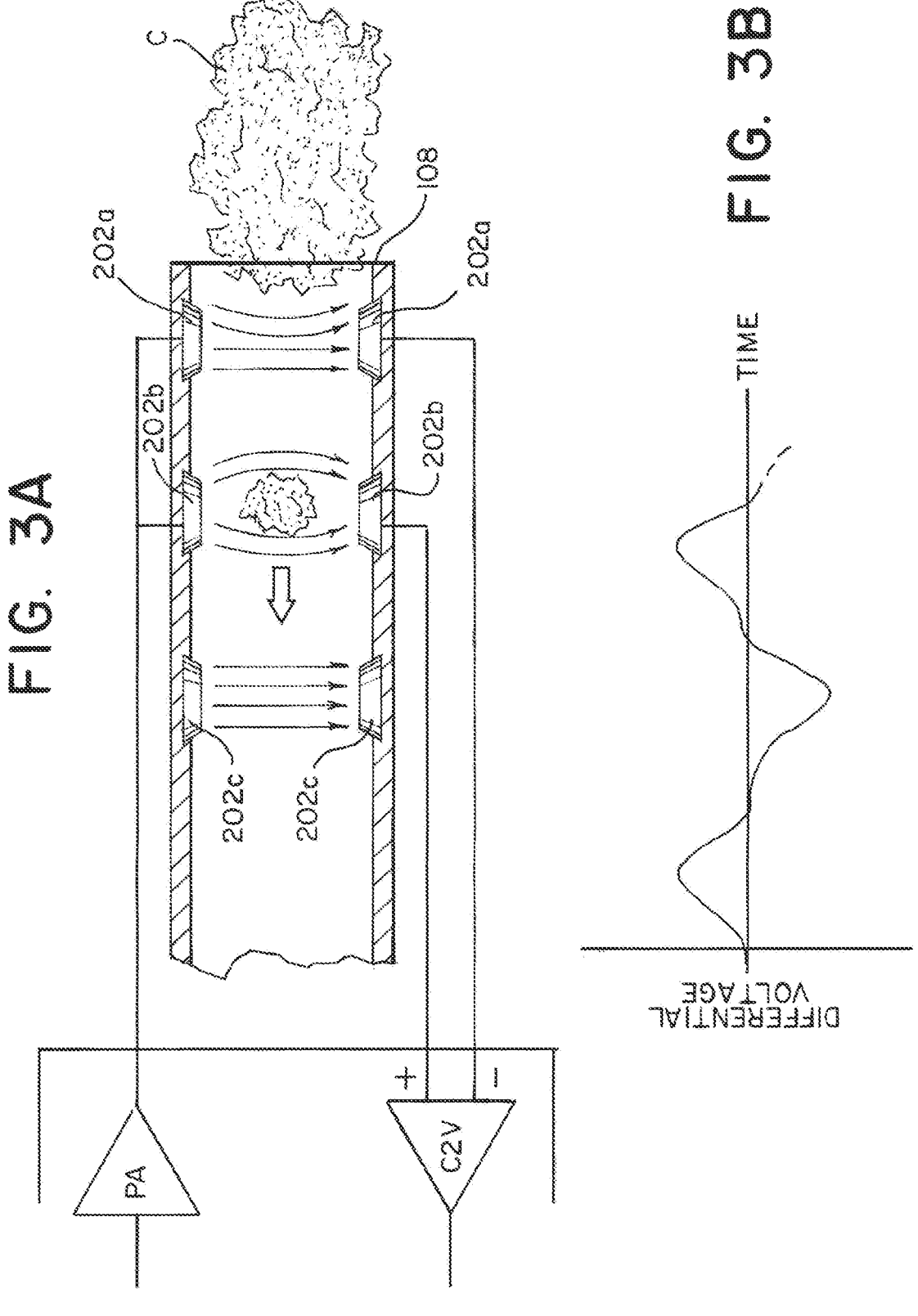
FIG. 3A provides a cross-sectional side view of an example clot receptor device, according to aspects of the present disclosure.
FIG. 3B provides an example waveform of a measured signal of FIG. 3A as an object passes between electrode pairs, according to aspects of the present disclosure.

FIG. 3A is a cross-sectional side view of an example aspiration catheter 102 showing one or more electrode pairs 202 in electrical communication with the control console 200. Arrows indicate current flow between electrode pairs. In some examples, the electrode pairs 202 may work by impendence measurements. Electrical connectors inside the wall of the catheter 102 can connect with an amplifier in the control console 200 and provide simulation voltage to one of the electrodes 202a in the electrode pair 202 and return electrical connectors can provide response currents from the second of the electrodes 202b in the electrode pair 202. FIG. 3B provides an example waveform of a measured signal as an object (of FIG. 3A) passes between electrode pairs (202a, 202b, and 202c of FIG. 3A). When a clot approaches the distal tip 108 of the catheter 102, the current flow between respective electrode pairs 202a, 202b, 202c can be altered such that a waveform of the measured current signal can be directly related to the dielectric properties of the object approaching or passing the electrode pairs 202a, 202b, 202c. Such measured current signal can indicate when a clot has entered the distal end 108 of the catheter 102 or whether the clot has yet to engage with the catheter 102. In addition, a series of electrode pairs 202 extending proximally within the inner lumen 104 of the catheter 102 can inform the medical professional as to how much clot has entered the catheter 102 as well as the composition or mechanical properties of such clot. In the event of a clot breakage (represented as the shape with dotted lines in FIG. 3A), impedance measurements from the series of electrode pairs 202 can inform the medical professional that the clot breakage has passed through the catheter. If a clot is slowly entering the distal tip 108 of the catheter 102, the progression of the clot movement can be measured by the series of electrode pairs 202 and provide feedback to the medical professional as the progression is being made. As would be appreciated by those of skill in the relevant art, real-time feedback of the composition and/or progress of clot aspiration during the procedure can be life-saving. For instance, if no progress is being made or the clot is just minimally engaged with the distal tip 108 of the catheter 102, the physician may choose to try a different method in combination with aspiration, e.g., deployment of a stentriever to better engage the clot or adjust the vacuum pressure or waveform pattern as described herein. In some instances, the measured current signal from the electrode pairs 202 in combination with the first, second, or third pressure sensors 204, 206, 208 can establish that the vessel has collapsed or that the distal end 108 of the catheter 102 has engaged with the vessel wall instead of the clot, informing the physician to adjust course.

Figures 4C, 6:
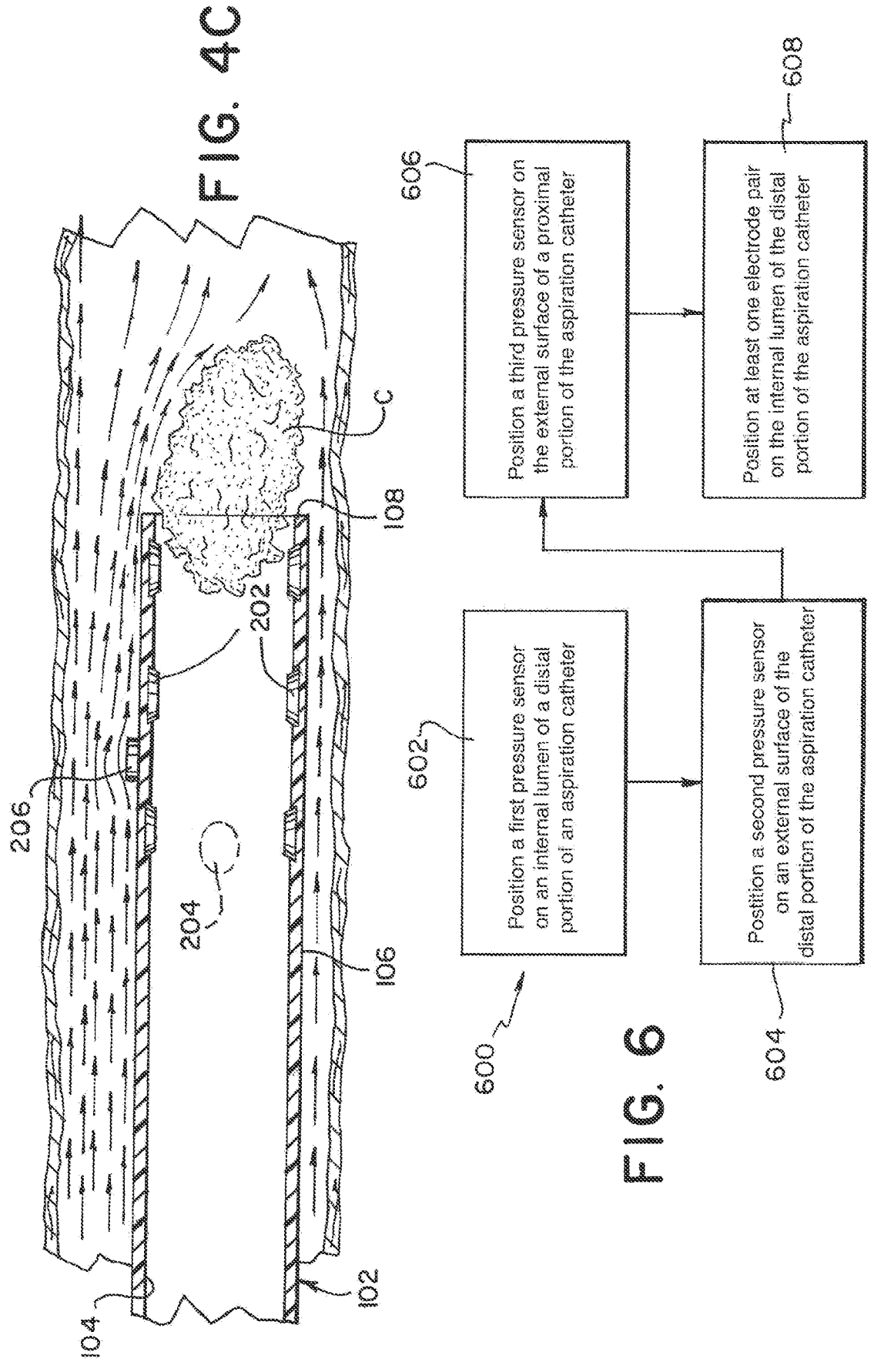

FIGS. 4A through 4C illustrate fluid dynamics in and around a clot receptor device as a clot approaches the catheter 102 (FIG. 4A) permitting fluid to continue to flow within the inner lumen 104; begins to engage with the catheter 102 (FIG. 4B) beginning to restrict flow within the inner lumen 104; and fully engages with the catheter 102 (FIG. 4C) such that flow is stopped within the inner lumen 104. The first pressure sensor 204 can be located within the inner lumen 104 along the distal portion 110 and in some instances, near the distal tip 108 of the aspiration catheter 102. The second pressure sensor 206 can be similarly located along the distal portion 110 and/or near the distal tip 108 of the aspiration catheter 102, but on the external surface 106. The first pressure sensor 204 can be used to measure the pressure of fluid within the catheter 102 prior to clot engagement, while the second pressure sensor 206 can measure the pressure of fluid flowing within the vessel. Dotted lines in FIG. 4A indicate signals that the first and second pressure sensors 204, 206 can simultaneously transfer to the control console 200, such as through the I/O communications interface 54. Comparing the distal internal pressure to the distal external pressure prior to clot engagement may be useful for establishing an antegrade flow rate around the catheter 102, which may indicate how occlusive the catheter is in the vessel. In addition to assisting in the antegrade flow rate measurement, the first pressure sensor 204 can be used to measure the pressure within the catheter 102 before, during, and after aspiration. Such measurements can provide valuable insight to the medical professional as to whether the clot is engaged with the distal tip 108 as the catheter 102 is advanced through the vessels. Alternatively, or in addition thereto, in the case of remote aspiration prior to the distal tip 108 of the catheter 102 engaging with the clot, the vacuum pressure from the aspiration pump 400, optionally in combination with aspiration waveform 60 administered of the control console 200, can be adjusted automatically or manually based on the reading of the first pressure sensor 204 within the inner lumen 104 of the catheter 102 to ensure the vessel does not collapse due to the difference in pressures within the catheter 102 and the vessel. Under such remote aspiration, a steady movement of the clot in the retrograde direction towards the distal tip 108 of the catheter 102 may be achieved.

When the catheter 102 approaches the clot, the catheter 102 may become near or fully occlusive in the vessel, as depicted in FIGS. 4B and 4C, respectively. At near occlusion, the first pressure sensor 204 can indicate a reduction in flow of fluid within the inner lumen 104 of the catheter 102 compared to the external pressure measured by the second pressure sensor 206. When the catheter 102 is fully occluded by the clot, the difference in pressure between the internal and external pressure sensors can indicate to control console 200 to prevent the first pressure sensor 204 from providing information for the blood pressure in the vessel and optionally transfer signal from the second pressure sensor 206.

During withdrawal of the catheter 102 with the clot fully engaged at the distal tip 108, the clot may resist removal and begin to slip out of the catheter 102. A combination of signals from the electrode pairs 202 and pressure sensors 204, 206, 208 may indicate the backing-out of the clot as a change in impedance and/or a change in pressure within the inner lumen 108 of the catheter 102. Control console 200 may alert the medical professional of such an event prior to the clot becoming dislodged from the distal tip 108. The alert may indicate to the medical professional to slow down or stop withdrawal to avoid losing the clot.

Referring back to FIG. 1, the combination of pressure sensors 206, 208 located on the exterior surface 106 of the catheter 102 along the distal portion 110 and the proximal portion 112 can provide signals to the blood pressure tracking module 56 of the control console 200. The third pressure sensor 208 positioned on the proximal portion 112 of the catheter 102 can signal to control console 200 information regarding a patient's systemic blood pressure when the third pressure sensor 208 is located near the patient's internal carotid artery (ICA). Information from this third pressure sensor 208 can be used to adjust the vacuum pressure, automatically through the control console 200 or manually, such that an aspiration waveform pattern and the vacuum pressure from the aspiration pump 400 matches the patient's blood pressure waveform pattern. In some examples, the aspiration waveform pattern can be adjusted to be in phase with the patient's blood pressure or out of phase with the patient's blood pressure.

Figure 5:
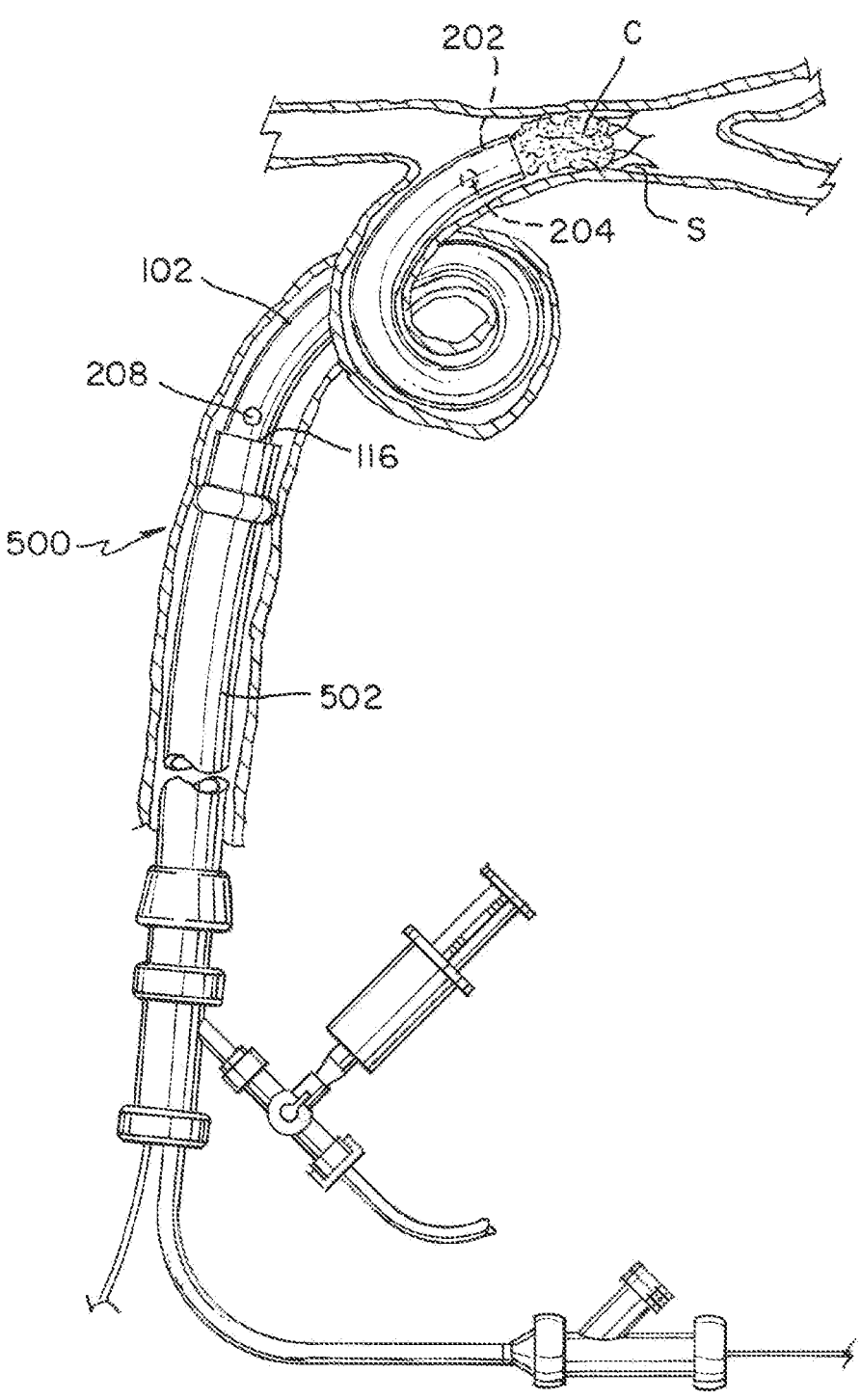
FIG. 5 illustrates an exemplary clot receptor system having an outer catheter and an inner aspiration catheter having sensors, according to aspects of the present disclosure.

FIG. 5 provides an exemplary clot receptor system 500 having an outer catheter 502 and an inner aspiration catheter 102 disposed in the lumen of the outer catheter 502. The inner aspiration catheter 102 can have electrode pairs 202 and pressure sensors 204, 206, 208. In some examples, the system 500 can further include a seal 116 located on the exterior surface 106 of the inner catheter 102. The seal can be configured to seal against the lumen of the outer catheter 502 such that an aspiration applied through the outer catheter 502 is transferred to the inner catheter 102. Although not depicted in FIG. 5, the system 500 can be also include the control console 200 connected to the electrode pairs and pressure sensors, as described herein. When the third pressure sensor 208 is positioned on the external surface 106 in the proximal portion 112 of the inner catheter 102 but outside the outer catheter 502, the third pressure sensor 208 can provide information regarding the effects on antegrade blood pressure near the ICA when an additional device is used, such as a balloon guide catheter or stentriever.

FIG. 6 is a flowchart illustrating a method 600 of manufacturing a clot retrieval system. Method 600 can include positioning 602 a first pressure sensor on an internal lumen of a distal portion of an aspiration catheter. Method 600 can further include positioning 604 a second pressure sensor on an external surface of the distal portion of the aspiration catheter. Method 600 can include positioning 606 a third pressure sensor on the external surface of a proximal portion of the aspiration catheter. Method 600 can send at step 606 or can further include positioning 608 at least one electrode pair on the internal lumen of the distal portion of the aspiration catheter.

As will be appreciated by one skilled in the art, method 600 can include any of the various features of the disclosed technology described herein and can be varied depending on the particular configuration. In some examples, methods of using the catheter manufactured by method 600 can include positioning the aspiration catheter near the clot within the vessel, aligning the third pressure sensor of the aspiration catheter with an exit of an outer catheter, equalizing the third pressure input with a waveform of a blood pressure of the patient, and applying, through the aspiration catheter, an aspiration waveform equal the waveform of the blood pressure of the patient.

While the present disclosure has been described in connection with a plurality of exemplary aspects, as illustrated in the various figures and discussed above, it is understood that other similar aspects can be used or modifications and additions can be made to the described aspects for performing the same function of the present disclosure without deviating therefrom.

Certain implementations of the disclosed technology are described above with reference to block and flow diagrams of systems and methods and/or computer program products according to example implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented or may not necessarily need to be performed at all, according to some implementations of the disclosed technology.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks.

Implementations of the disclosed technology may provide for a computer program product, having a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

It will be apparent from the foregoing description that while particular embodiments of the present invention have been illustrated and described, various modifications can be made without departing from the spirit and scope of the invention. For example, while the embodiments described herein refer to particular features, the invention includes embodiments having different combinations of features. The invention also includes embodiments that do not include all of the specific features described. The invention is not limited to the embodiments hereinbefore described which may be varied in construction and detail.

What is claimed is:

1. An aspiration catheter for assisting in retrieval of a clot from a vessel of a patient, the aspiration catheter comprising:
  at least one electrode pair positioned on a first side of a wall that defines an inner lumen of the aspiration catheter, the inner lumen extending proximal along a longitudinal axis between a distal tip and a proximal hub;

a first pressure sensor positioned at a distal portion proximal the distal tip and within the inner lumen of the aspiration catheter;

a second pressure sensor positioned at a distal portion proximal the distal tip on an opposed side of the wall that defines an exterior surface of the aspiration catheter;

a third pressure sensor positioned at a proximal portion of the aspiration catheter on the exterior surface of the aspiration catheter; and a seal located on an exterior surface of the aspiration catheter, the seal being configured to seal against the lumen of an outer catheter such that an aspiration applied through the outer catheter is transferred to the aspiration catheter.

2. The aspiration catheter of claim 1, wherein:

the at least one electrode pair is configured to transmit an electrical input to a control console, wherein the electrical input comprises a change in conductivity in a fluid flowing inside the inner lumen of the aspiration catheter.

3. The aspiration catheter of claim 2, wherein:

when the distal tip of the aspiration catheter is near the clot, the at least one electrode pair is configured to detect the clot within the fluid flowing inside the inner lumen of the aspiration catheter.

4. The aspiration catheter of claim 1, wherein:

when the distal tip of the aspiration catheter is engaged with the clot, the at least one electrode pair is configured to monitor the clot as the aspiration catheter is moved about the vessel.

5. The aspiration catheter of claim 1, wherein:

the first pressure sensor is configured to transmit a first pressure input to a control console;

the second pressure sensor is configured to transmit a second pressure input to the control console; and the third pressure sensor is configured to transmit a third pressure input to the control console, wherein the first, second, and third pressure inputs are different.

6. The aspiration catheter of claim 5, wherein:

when the distal tip of the aspiration catheter is near the clot, the first pressure input and the second pressure input together generate a pressure measurement of an antegrade flow rate around the aspiration catheter in the vessel.

7. The aspiration catheter of claim 5, wherein:

the control console is further configured to modulate an aspiration by applying an oscillating vacuum waveform based on pressure input from one or more pressure sensors.

8. The aspiration catheter of claim 5, wherein:

the control console is further configured to modulate an aspiration to a waveform of a blood pressure of a patient by applying an oscillating vacuum waveform in phase with a blood pressure waveform of the patient.

9. The aspiration catheter of claim 5, wherein:

the control console is further configured to modulate an aspiration to a waveform of a blood pressure of a patient by applying an oscillating vacuum waveform out of phase with a blood pressure waveform of the patient.

* * * * *